United States Patent [19]

Dawson et al.

[11] 4,277,970

[45] Jul. 14, 1981

[54] APPARATUS AND METHOD FOR SPECIFIC GRAVITY MEASUREMENT

[76] Inventors: Paul R. Dawson, 256 Renwick Dr., Ithaca, N.Y. 14850; Gregg W. Dawson, 1160 S. Madison St., Denver, Colo. 80210

[21] Appl. No.: 119,033

[22] Filed: Feb. 6, 1980

[51] Int. Cl.³ .......................... G01N 9/08; G01N 9/22
[52] U.S. Cl. ..................................... 73/32 R; 73/433
[58] Field of Search .......................... 73/32 R, 433–43, 73/4, 437, 444, 445

[56] References Cited

U.S. PATENT DOCUMENTS

| | | | |
|---|---|---|---|
| 2,348,733 | 5/1944 | Fischer | 73/32 |
| 2,800,019 | 7/1957 | Rumble | 73/32 X |

Primary Examiner—James J. Gill
Attorney, Agent, or Firm—Young & Martin

[57] ABSTRACT

Apparatus and method for specific gravity measurement of an object having a known geometry and weight is provided which is particularly adaptable for determining the specific gravity of a gemstone. The apparatus includes a fluid circuit and a pump therefor with the fluid circuit having an adjustable fluid flow rate. The fluid circuit also includes a test chamber element for receiving the object and a flow measuring element for determining fluid flow rate. Preferably, the test chamber is vertically oriented and has zones of decreasing fluid velocity from its lower to upper ends for a constant fluid flow rate through the circuit. The method of measurement is made in one of two modes. In one mode, the flow rate is held constant so that the vertical position of the object of unknown specific gravity in the test chamber yields data allowing calculation of its specific gravity. In the second mode, the fluid flow rate is adjusted so that the object attains an equilibrium position at a pre-selected location in the test chamber and the fluid velocity at that point is then determined by measuring the flow rate through the fluid circuit and the specific gravity is thereby calculated.

24 Claims, 11 Drawing Figures

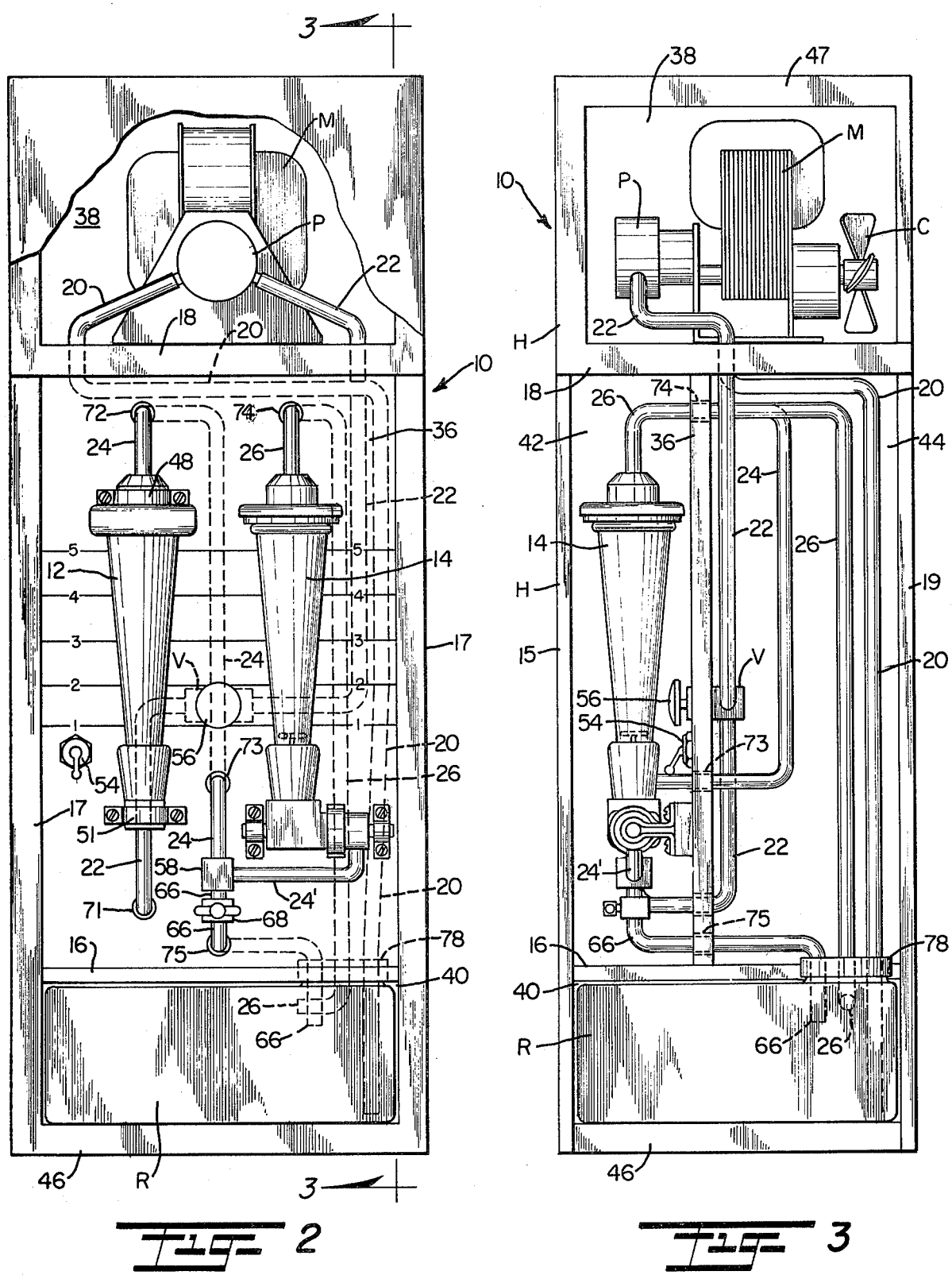

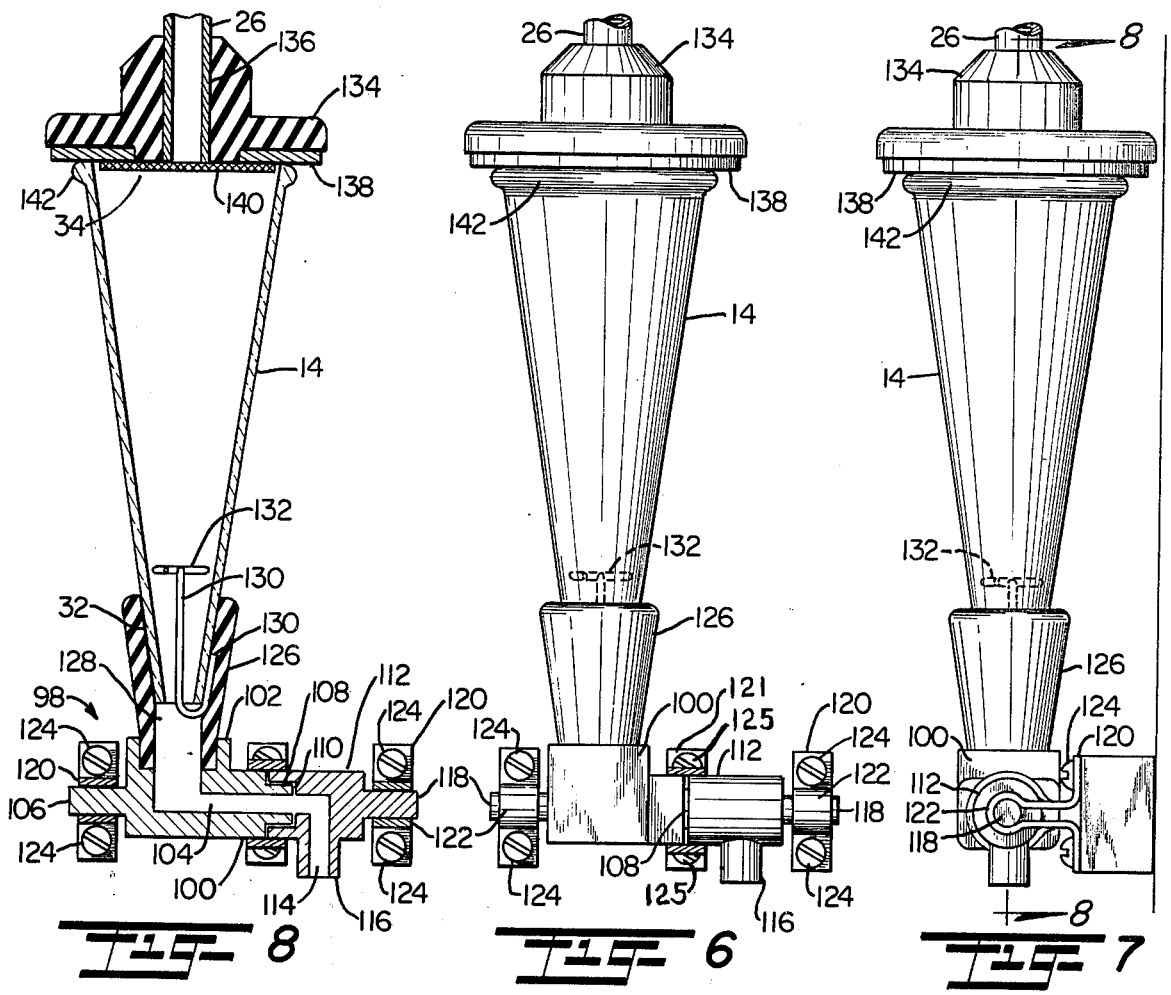

APPARATUS AND METHOD FOR SPECIFIC GRAVITY MEASUREMENT

BACKGROUND OF THE INVENTION

This invention relates to an apparatus and method for determining the specific gravity of materials and more specifically to a method and apparatus for measuring the specific gravity of gemstones and the like.

An important aspect of the trade of a jeweler or a gemologist resides in the ability to determine the identity and value of a gemstone. While numerous parameters require analysis in the determination of a stone's identity, such as, the color, weight, flaw characteristics, and the like, one of the more important physical characteristics used in evaluating a gemstone is its specific gravity. This particular measurement is important because specific gravities of the major gemstones seldom overlap. Hence, this measurement provides a useful tool in distinguishing among differing types of gemstones and identifying counterfeit or synthetic gemstones.

While several techniques to measure specific gravity of gemstones have been developed in the past, most importantly, the use of heavy liquids and the hydrostatic process, jewelers and other persons desiring to measure specific gravity have thus far not been able to apply these methods in a sufficiently accurate fashion to make the specific gravity an accurate tool for analyzing the gemstone. Problems such as expense, difficulty in performing the measurements, and inaccuracy have made these techniques prohibitive for normal use at the retail level. A description of these heavy liquid and hydrostatic techniques may be found in R. Webster, Gems 566-82 (3ed. 1975), and the review of this material demonstrates the difficulties a jeweler would encounter in attempting to measure specific gravity of a gemstone according to these processes.

While the hydrostatic method typically yields a measurement having a greater accuracy than the heavy liquid method, this method needs a very sensitive balance, substantial calculation and substantial time in performance. A drawback of the hydrostatic method is that it is not effective in measuring the specific gravity of smaller specimens. The reason for this drawback is that the drag factor caused by the surface tension of the water can introduce substantial error in the measurement of specific gravity, particularly where the gemstone weighs less than five carats. This weight category includes a large majority of all gemstones. A quicker, though less accurate measurement for smaller gemstones can be made using a heavy liquid floatation method. However, due to the high density of the liquids required for this approach, a disadvantage is introduced since many of the high density liquids are poisonous and expensive. In addition, the heavy liquid method yields only a specific gravity range and not an exact value for the gemstone tested.

As a result of the difficulties referred to above, there is a need for an inexpensive yet accurate apparatus and method for determining the specific gravity of a gemstone with this apparatus being of a nature susceptible to utilization by a person untrained in sophisticated techniques for specific gravity measurement.

SUMMARY OF THE INVENTION

It is therefore an object of the present invention to provide a novel method and apparatus for determining the specific gravity of an object such as a gemstone in a manner that is quick, inexpensive and capable of being utilized by persons having limited or no training with regard to traditional techniques of specific gravity measurement.

A further object of the present invention is to provide an apparatus wherein a gemstone of unknown specific gravity may be placed in an upwardly flowing fluid stream such that the gravitational force acting on a gemstone becomes balanced with the gemstone's drag force in that fluid thereby yielding data relevant to a determination of that gemstone's specific gravity.

A still further object of the present invention is to provide a method and apparatus wherein a gemstone of known weight is placed in an upwardly flowing stream of fluid wherein the velocity of the fluid is a function of height so that the equilibrium position of the gemstone indicates the specific gravity thereof.

Yet another object of the present invention is to provide an apparatus wherein a closed fluid circuit is provided through which a viscous fluid is circulated with a portion of that flow being upwardly directed through a vertical portion of that circuit such that the velocity of the fluid in that vertical portion is a function of height therein so that the velocity of the fluid may be adjustably regulated to establish an equilibrium position of the gemstone in the vertical portion which is indicative of its specific gravity.

The method according to the present invention permits measurement of an unknown specific gravity of a gemstone having a standard geometrical cut and having a known weight with this measurement being accomplished by the positioning of the sample gemstone in a vertically upward flowing stream of viscous fluid. By adjusting the rate of flow of the fluid, the downwardly directed force of gravity acting on the stone may be balanced with the drag force on it in the flowing fluid so that by determining the velocity of the fluid necessary to maintain a specific, selected equilibrium position, the specific gravity of the stone may be deduced. Hence, the method requires both a balancing of these two forces while quantitatively measuring the rate of fluid flow past the sample gemstone. Preferably, a fluid flow system is provided such that velocity of fluid past the gemstone is proportional to its vertical position so that direct measurements may be simplified. This method may be practiced in two basic modes as discussed below.

Apparatus is provided to perform the steps of measuring the specific gravity of a gemstone. In the preferred embodiment a pair of tapered tubes are vertically oriented with the tapered sidewalls being upwardly divergent. These chambers are connected to a fluid circuit so that fluid is passed through the tapered tubes which are vertically oriented with the tapered sidewalls being upwardly divergent so that fluid is passed through the tubes from their bottom ends to their upper ends. One of the tubes, the flow control tube, serves as a measuring device for fluid velocity while the other of the tubes provides the test chamber for the sample gemstone. The fluid velocity in the fluid circuit is adjustably regulated so that the gemstone in the test chamber can be placed in an equilibrium position and the fluid velocity can then be determined from the other of the tapered tubes.

This preferred apparatus permits the practice of the method of measurement in two basic modes. First, for the measured weight of the gemstone of unknown specific gravity, a constant rate of fluid flow through the fluid circuit can be maintained, for example, by adjusting the equilibrium position of the float stone to a location in its tube corresponding to the weight of the unknown gemstone. Since, in the preferred embodiment of the apparatus, the test chamber is constructed so that the fluid velocity is greatest at its base, the equilibrium position of the unknown gemstone then indicates its specific gravity. The second mode of operation is practiced by altering the flow rate through the fluid circuit until the unknown stone reaches an equilibrium position at a selected location in the test chamber. By then determining the fluid velocity of the fluid at that location, and by knowing the weight of the unknown stone, the specific gravity of the unknown stone may readily be calculated. The fluid velocity is easily ascertainable by examining the position of a float in the flow control tube.

These and other objects of the invention will become more readily appreciated and understood from a consideration of the following detailed description of the preferred embodiment when taken together with the accompanying drawings, in which:

BRIEF DESCRIPTION OF THE DRAWINGS

FIG. 2 is a front view in elevation of the preferred embodiment of the apparatus according to the present invention;

FIG. 3 is a cross-sectional view taken about lines 3—3 in FIG. 2;

FIG. 6 is a front view and elevation of the test chamber according to the preferred embodiment of the present invention;

FIG. 7 is a side view in elevation of the test chamber shown in FIG. 6;

FIG. 8 is a cross-sectional view of the test chamber shown in FIGS. 6 and 7;

FIG. 9 is an alternate embodiment of the fluid flow tube according to the present invention;

FIG. 10 is a second alternate embodiment of the fluid flow tube according to the present invention;

FIG. 11 is still another embodiment of the fluid flow tube according to the present invention.

DETAILED DESCRIPTION OF THE PREFERRED EMBODIMENT

Figure 1:
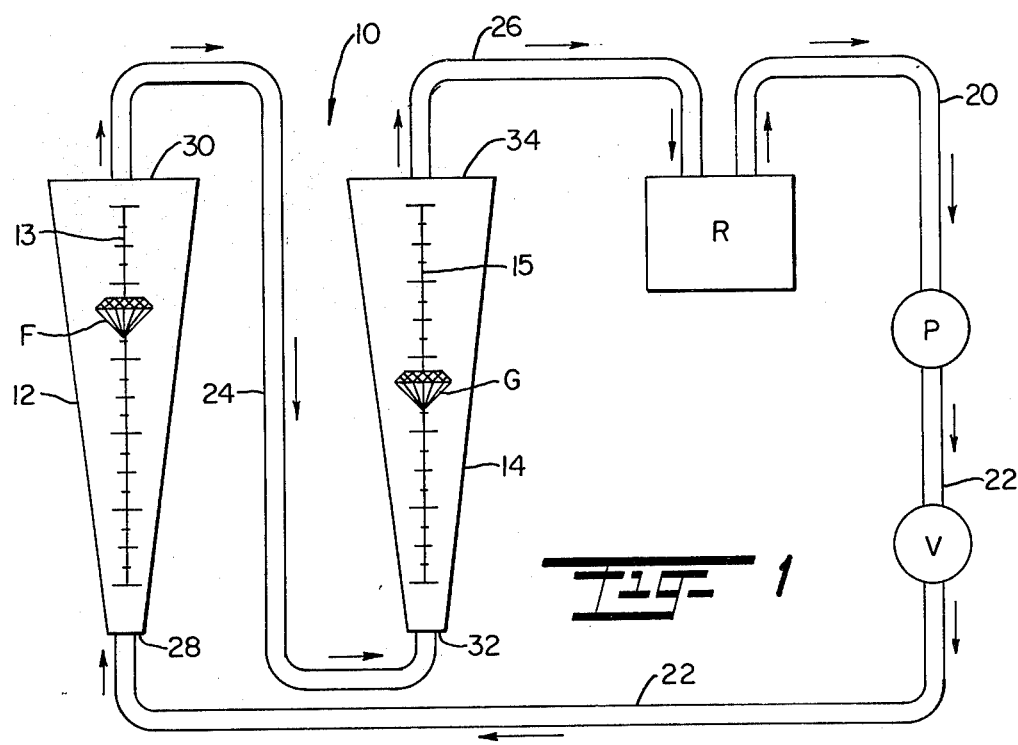
FIG. 1 is a diagrammatic representation of the fluid circuit of the gemstone specific gravity device according to the present invention.

As noted above, the present invention includes the method and apparatus for measuring an unknown specific gravity of a sample gemstone. Broadly, the method includes the balancing of the buoyant and gravity forces acting on a gemstone with the drag force acting on the gemstone when it is placed in a vertically upwardly moving stream of fluid, and is operable in two basic modes to be discussed below. In general, however, the velocity of the fluid necessary to establish an equilibrium between these forces, then, in cooperation with other parameters of the gemstone, allow a determination of its specific gravity.

The theory of operation of the present invention is understandable from consideration of two basic equations of fluid dynamics. When an object is placed in a fluid, gravity acts on that object in the normal manner except that the object displaces a volume of fluid equal to its own volume so that the weight of the displaced fluid must be accounted for in the general force equation. The resultant force acting on the object is known as the buoyant force, and it is mathematically expressed:

$$F_b = (S_o - S_f)\gamma_w V_o$$

where:
$S_o$ = specific gravity of the object
$S_f$ = specific gravity of the fluid
$\gamma_w$ = specific weight of water
$V_o$ = volume of the object.

However, when the fluid is placed in motion, a second important force acts on the object, namely, the drag force, and this may be expressed:

$$F_d = K v_f A_o$$

where:
K = a proportionally constant
$v_f$ = velocity of the fluid
$A_o$ = largest cross-sectional area of the object normal to the direction of fluid flow.

If the fluid is caused to flow vertically upward, that is, in a direction opposite the resultant gravity force, the forces will oppose one another in the typical case where the object has as specific gravity greater than that of the fluid. In this case, by varying the fluid flow, the object may be placed in a state of equilibrium, and, in this state:

$$F_b = F_d; \text{ thus}$$

$$(S_o - S_f)\gamma_w V_o = K v_f A_o$$

Solving for fluid velocity:

$$v_f = \frac{(S_o - S_f)\gamma_w V_o}{K A_o}$$

From this, it should be appreciated that, for an object of fixed size, that is, for fixed $V_O$ and $A_O$, the fluid velocity must increase and decrease in proportion to the object's specific gravity. Likewise, where two objects have the same specific gravity, similar geometrical shapes and different weights, the larger of the objects will have a larger $V_o/A_o$ ratio and will therefore require a greater fluid velocity to reach a state of positional equilibrium.

When considering gemstones, for each type of material there exists a limited range of proportions for standard "cuts". For each of these cuts, a gemstone can be larger or smaller than another gemstone of the same cut, but the shapes are geometrically similar since corresponding facets on each stone are oriented at the same angle with its adjacent faces with a fairly low error factor. Thus, the $V_o/A_o$ ratio is linear, so that, where stones have identical specific gravities, a stone having a measured dimension twice the magnitude of the corresponding dimension of a second stone will have double the $V_o/A_o$ ratio of the second stone. These conditions permit a relatively simple method of measurement of specific gravity as will be described in conjunction with the preferred embodiment of the apparatus set forth below.

Specifically, the preferred embodiment of the apparatus for measuring the specific gravity of a gemstone is shown in FIGS. 1-5 in which FIG. 1 is a diagrammatical view of the circuit designed for measurement of specific gravity. As shown in FIG. 1 measurement device 10 defines a closed fluid circuit including pump P, valve V and reservoir R as well as fluid flow tubes 12 and 14, one of which functions as a flow control tube and the other of which functions as a test chamber. As can be seen in FIG. 1, circulating pump P is connected to reservoir R by means of conduit 20, and pump P forces the fluid, such as water, through conduit 22 to a lower end 28 of flow tube 12. Conduit 22 is interrupted by valve V so that valve V can be used to regulate the amount of fluid flowing through conduit 22. The second end 30 of flow tube 12 is connected to a conduit 24 which in turn is connected to lower end 32 of flow tube 14. The upper end 34 of flow tube 14 is then connected to conduit 26 which returns the fluid to reservoir R to complete the fluid circuit. According to this invention, float F, preferably a standard gemstone of known physical characteristics, is positioned in tapered tube 12. Another gemstone of unknown specific gravity but known weight can be placed in a flow tube 14, and its specific gravity can be measured according to the method of this invention by adjusting the flow rate of fluid in the system to a rate corresponding to the weight of the gemstone G on a pre-determined scale 13 on flow tube 12 and reading the specific gravity at the position of the gemstone G on a pre-determined scale 15 on flow tube 14. The interrelationship between float F, gemstone G, and the scales 13 and 15 on flow tubes 12 and 14, respectively, in measuring specific gravity of the gemstone G will hereinafter be described in greater detail.

The preferred construction of the novel gemstone apparatus according to the present invention is shown in greater detail in FIGS. 2 and 3. The measurement device 10 is shown in FIGS. 2 and 3 according to the present invention and includes a housing H which supports the components of the system. Housing H is formed as a generally rectangular enclosure having a hinged door 15, a pair of sidewalls 17, a base 46 and a top wall 47. Housing H supports a pair of horizontal shelves 16 and 18 as well as a vertically oriented interior wall 36. Shelves 16 and 18 generally divide housing 10 into three compartments: An upper compartment 28, a lower compartment 40, and a middle compartment which is divided by interior wall 36 into forward compartment 42 and rear corridor 44. Upper compartment 38 contains pump P and a motor M with its associated cooling fan C with these elements being mounted in any convenient manner to shelf 18. Lower compartment 40 communicates with corridor 44 supporting reservoir R with reservoir R resting on bottom wall or base 46 of housing H.

Flow tubes 12 and 14 are mounted against interior wall 36 which is oriented vertically when base 46 rests on a suitable support surface. Flow tube 12 is mounted to interior wall 36 by means of a pair of brackets 48, and flow tube 14 is mounted to interior wall 36 by brackets. The specific mounting of flow tubes 12 and 14 will, however, be described in more detail with respect to FIGS. 4 through 8 below. Interior wall 36 also supports a switch 54 and valve member V in any convenient manner. Switch 54 is electrically connected to motor M to activate and deactive the same although the specific wiring for this electrical connection is not shown. Valve V, positioned in corridor 44, interrupts conduit 22 as a standard metering valve so as to regulate flow of fluid through the fluid circuit. Valve V has a sprocket 56 which projects therefrom with sprocket 56 passing through a hole in interior wall 36 so that the enlarged end of sprocket 56 may be accessible for manual adjustment. It should be noted that the fluid velocity could also be conveniently regulated by attaching a rheostat to motor M and eliminating valve V. This rheostat could readily increase and decrease the operating speed of pump P to vary the fluid flow rate.

A drain assembly is provided at the lower end of flow tube 14 to allow the drainage of fluid therefrom when the apparatus is not in use. Specifically, conduit 24 is interrupted by T-connector 58 at a position forward of interior wall 36. T-connector 58 has two branches, that is, it is in fluid communication with a conduit 24' and a tube 66. Tube 66 is interrupted by a stopcock 68 which may be placed in an on or off position to allow or prevent flow of fluid therethrough. Conduit 24' is an extension of conduit 24 and is connected to flow tube 14 through swivel bracket assembly 98 described below. Tube 66 extends from stopcock 68 to reservoir R so that, when stopcock 68 is opened, fluid may drain from flow tube 14 through T-connector 60 and into reservoir R. Since reservoir R has a greater capacity than the flow circuit, the opening of stopcock 68 tends to siphon the fluid out of flow tube 12 as well.

It should be noted that rear corridor 44 is provided to allow the positioning of the various conduits according to the present invention and, since several of these conduits must be connected to elements on the opposite side of interior wall 36, a plurality of bores 71-75 are provided to accommodate connection of these conduits. Five such bores are provided and, in addition, a hole, not shown, is provided in interior wall 36 to allow the enlarged knob of sprocket 56 to be mounted into valve V.

The conduit network may now be more thoroughly described with respect to FIGS. 2 and 3. Specifically, conduit 20 extends from reservoir R with an open end 80 positioned near the bottom of reservoir R adjacent base 46. Conduit 20 then extends upwardly where it passes through a bore in horizontal shelf 18 to be connected to pump P. Conduit 22 is connected to the opposite side of pump P and extends through a second bore in horizontal shelf 18 and downwardly to be connected to one side of valve V. Conduit 22 then continues from the second side of valve V to extend first downwardly through a lower bore 71 and then upwardly for connection to flow tube 12 on the opposite side of interior wall 36. Conduit 24 extends from the upper portion of flow tube 12 and passes through bore 72 so that it enters corridor 44. Conduit 24 then extends downward to bore 73 and again passes to the exterior side of interior wall 36 through bore 72 and is connected to T-connector 58. Conduit 24' interconnects a lower end of flow tube 14 and conduit 24 through T-connector 58. Conduit 26 is connected to the upper end of flow tube 14 and extends rearwardly through bore 74 and into corridor 44 after which it extends downwardly to an exhaust opening in reservoir R. Finally, tube 66, which connects flow tube 14 with reservoir R for drainage, extends from outwardly projecting stopcock 68 through bore 75 and into an exhaust bore position in reservoir R. It should be appreciated that tube 66 as well as conduits 26 and 20 may extend through a common cap 78 of reservoir R or could be connected in any other convenient manner to reservoir R. However, it is preferrable that conduits 20 and 26 as well as tube 66 should be readily detachable from reservoir R so that reservoir R can be removed from the assembly and filled with fluid prior to the activation of measurement device 10.

Figures 4, 5:
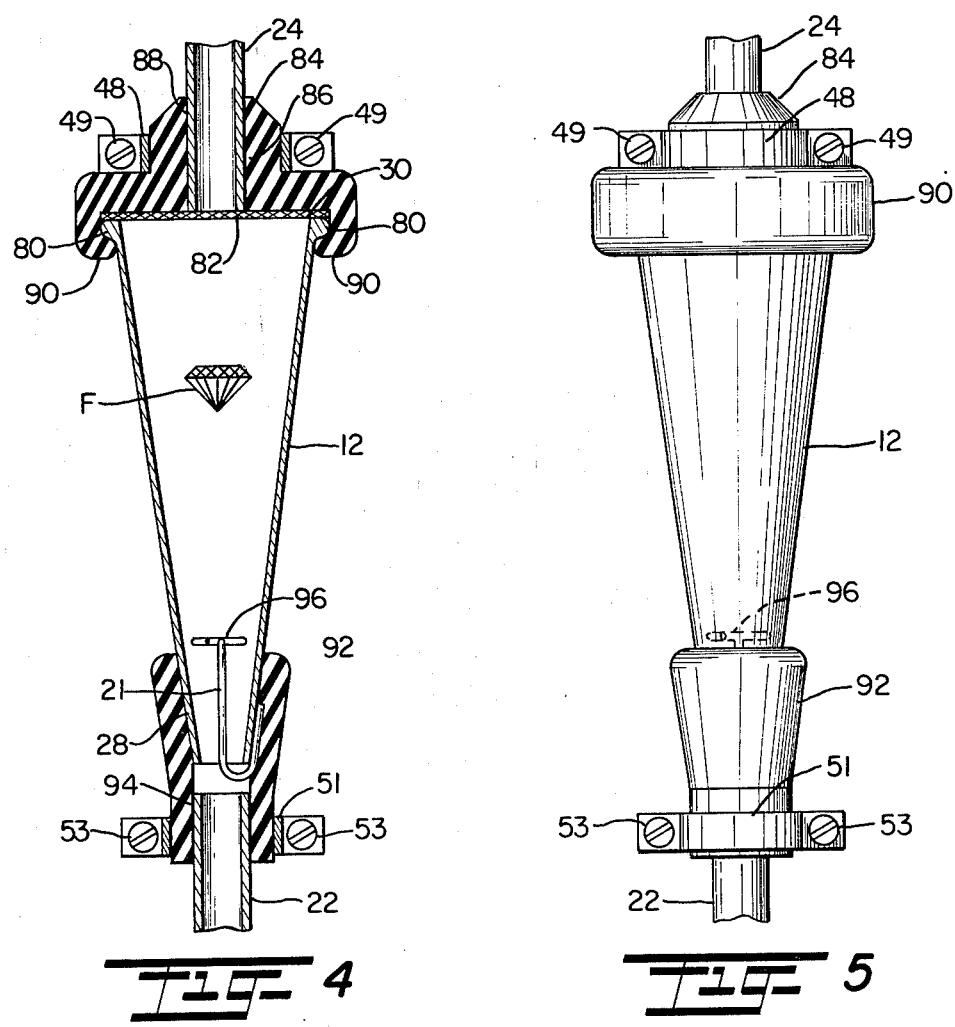
FIG. 4 is a front view in elevation of the flow control tube according to the preferred embodiment of the present invention.
FIG. 5 is a cross-sectional view of the flow control tube shown in FIG. 4.

Flow tube 12 is shown in greater detail in FIGS. 4 and 5, and flow tube 14 is shown in greater detail in FIGS. 6–8. Flow tube 12, as shown in FIGS. 4 and 5, is in the form of an inverted, elongated frustum with upwardly divergent walls and a circular cross-section of constantly increasing cross-section from the bottom to the top. The upper end 30 of flow tube 12 is open and includes a surrounding rim 82 which projects outwardly therefrom. A screen 82 is positioned across the top of open end 30, and a rubber seal 84 is adapted to be secured to upper end 30 of flow tube 12. Rubber seal 84 includes a main body 86 which has a hole 88 passing longitudinally therethrough. Hole 88 receives conduit 24 in fluid-sealed relation thereto. In addition, rubber seal 84 includes an inwardly projecting lip 90 which is adapted to extend around rim 89 of flow tube 12 so as to sealably engage the upper portion thereof. In this manner, the upper open end 30 of tube 12 is sealed with screen 82 retained between main body 86 of seal 84 and rim 80. Rubber seal 84 is then attached to interior wall 36 by means of a bracket 48 and screws 49.

Lower end 28 flow tube 12 is mounted by means of rubber stopper 92. Rubber stopper 92 includes a longitudinal hole 94 so that rubber stopper 92 frictionally engages a lower portion of tube 12. Hole 94 also frictionally receives conduit 22 in sealed relation thereto. A screen 96 is positioned in a lower portion of flow tube 12, and is supported by a J-shaped wire 21 which, in turn, is frictionally secured in position between rubber stopper 92 and the sidewall of flow tube 12. Screen 96 is located sufficiently high in flow tube 12 to prevent float F from becoming lodged in the narrow tapered portion near the bottom of flow tube 12. Stopper 92 may then be mounted to interior wall 36 by means of a second bracket 51 and screws 53.

FIGS. 6–8 show flow tube 14 in greater detail and it should be understood that flow tube 14 is adapted to be a test chamber for the gemstone of unknown specific gravity. In a manner similar to that with respect to flow tube 12, flow tube 14 is formed so that it is upwardly divergent and, as shown in FIGS. 6–8 is formed as an inverted, elongated frustum. Tube 14 is pivotally mounted to interior wall 36 by means of a pivot or swivel bracket assembly 98. Swivel bracket 98 includes a swivel member 100 having an upstanding rim 102 and a passageway 104 adapted to pass fluid therethrough. Swivel member 100 includes a cylindrical projection 106 on one side, and a nipple 108 on the opposite side thereof. Nipple 108 is matingly received in bore 110 formed in coupling 112, and coupling 112 includes a passageway 114 which is in fluid communication with passageway 104 and makes a right angled turn to terminate in nipple 116 formed on coupling 112. Nipple 116 in turn is sized to frictionally connect with conduit 24. A cylindrical projection 118 is formed on a side of coupling 112 opposite bore 110.

Swivel bracket assembly 98 is mounted to interior wall 36 by means of a pair of brackets 120 which include an upper circular portion 122 adapted to receive cylindrical projections 106, 118 with brackets 120 being mounted to wall 36 by means of screws 124. It should be appreciated that cylindrical projections 106 and 118 form an axle on which swivel member 100 may rotate. Assembly 98 is also supported at the junction of swivel member 100 and coupling 112 by bracket 121 which is mounted to wall 36 by screws 125. In the construction of the preferred embodiment, however, coupling 112 is held rigid in any convenient manner so that swivel member 100 may rotate about the junction of cylindrical projection 106 and nipple 108. That is, cylindrical projection 106 rotates in bracket 120 while nipple 108 rotates in bore 110. To this end, it is necessary that a fluid seal be maintained between swivel member 100 and coupling 112, and this seal may be made by any convenient fluid seal as is known in the art.

Because it is necessary to open and close flow tube 14 to position the gemstone G to be measured therein and remove it when its specific gravity has been determined, flow tube 14 is mounted to swivel member 100 by means of rubber stopper 126 which has an elongated bore 128 formed therein. Bore 128 receives lower end 32 in frictionally secured relation. In addition, a J-shaped wire 130 extends around lower end 32 of flow tube 14 so that a leg of wire 130 is frictionally retained between lower end 32 and rubber stopper 126. The upper leg of J-shaped wire 130 has, at its upper end, a transversely extending circular screen 132 which is positioned to prohibit exit of a stone placed in flow tube 14, and is positioned at a portion of flow tube 14 having a fairly large diameter with respect to a typical gemstone so that it prevents a gemstone from becoming frictionally lodged in the narrow portion of flow tube 14 located below screen 132. It should be understood that any convenient screen may be used in place of screen 132 and J-shaped wire 130 to accomplish this purpose.

The upper end of flow tube 14 as shown in FIGS. 6–8 is sealed by means of a rubber stopper 134 which has a bore 136 passing therethrough. Bore 136 receives conduit 26 for fluid communication. A washer-like seal 138 of a suitable fluid seal material is seated around the perimeter of rubber stopper 134 and is adapted to abut the upper rim of flow tube 14 so as to define a fluid seal around the rim of the flow tube. Seal 138 supports a screen 140 which extends transversely across flow tube 14 adjacent the mouth of conduit 26 so as to prevent a sample gemstone from exiting the tube. Flow tube 14 has a shoulder or rim 142 at its upper mouth or upper end 34. Seal 138 is sandwiched between rim 142 and rubber stopper 134 so as to define a fluid seal, and stopper 134 is maintained in sealed relation to flow tube 14 by means of a conventional clamp (not shown) as is well known in the art.

It should be understood that, by constructing the test chamber represented by flow tube 14 in the above described manner, it is pivotal about the vertical interior wall 36. To accomplish this it is necessary that the fluid seal at the top of flow tube 14 be releasable so that the pivoting may take place. The releasable fluid connection of conduit 26 to flow tube 14 coupled with the ability for flow tube 14 to tilt outwardly and downwardly away from interior wall 36 provides a manner in which test sample may be conveniently removed after its specific gravity has been determined. It should also be appreciated that flow tube 12, and its associated conduit connection, could be constructed in an identical manner to that described with reference to FIGS. 6–8 so that flow tube 12 would be pivotal as well. This, then, would allow for removal of both the test sample as well as the control float. This capability is desired since it may be convenient to use a gemstone of known specific grivity as float F.

It should also be appreciated that this device could incorporate a temperature sensing and control means to determine the temperature of the fluid in flow tube 14, although no such means is shown in the Figures, since it is sometimes desirable to control or measure this parameter. Likewise a level may be provided to orient the device in the horizontal and vertical planes. Such a level is also not shown in the Figures, its incorporation being thought to be a simple matter of mechanical skill.

FIGS. 9-11 show alternate embodiments of construction for flow tubes 12 and 14. FIG. 9 discloses a flow tube having three stages of divergent sidewalls. Specifically, a flow tube 160 having a lower end 162 and an upper end 164 is shown with upper end 164 having a surrounding rim 166 which permits attachment of either of rubber stoppers 134 or 92. The flow tube 160 has a lower stage 168, a middle stage 170 and an upper stage 172. Each of the stages have sidewalls that are upwardly divergent, the difference between the stages being that the angle of divergence increases in ascending order. In other words, the angle of divergence of the sidewalls of upper stage 172 exceeds the angle of divergence for the sidewall of middle stage 170 which in turn is greater than the angle of divergence of the sidewall of lower stage 168. However, flow tube 160 has a circular cross-section taken about any transverse plane thereto.

FIG. 11 discloses yet another flow tube 174 which has a lower end 176 and an upper end 178 which is surrounded by a rim 180 which functions in a manner similar to that described with respect to flow tubes 12 and 14. Flow tube 174 has a circular cross-section and sidewalls which diverge as a function of the square root of the height above end 176, that is, the sidewalls are parabolic. Thus, the radius increases in proportion to the square root of the height in tube 174 so that the cross-sectional area of the tube at a given vertical location is linearly proportional to that vertical height. Because of this structure, a volume of water flowing through flow tube 174 will have a velocity that varies linearly as the fluid moves upwardly therethrough.

FIG. 10 shows yet another embodiment for a flow tube which may be employed with the present invention. In FIG. 11, flow tube 180 has a lower end 182 and an upper end 184 which is surrounded by a rim 186 which functions in a manner described with respect to flow tubes 12 and 14. Flow tube 180 is a combination of flow tubes 160 and 174 in that it includes a plurality of stages having divergent sidewalls, that is, frustoconical sidewalls, and a plurality of stages that are cylindrical. Specifically, a first cylindrical stage 188 is constructed at the lower end of flow tube 180 and adjoins a lower frustoconical stage 190 which has an upwardly divergent sidewall. It should be appreciated that the lower end of lower stage 190 is of the same dimension as that of lower cylindrical stage 188. A second or middle cylindrical stage 192 adjoins the upper portion of the frustoconical stage 190 and is of a common diameter therewith. A second or middle frustoconical stage 194 having a lower end of common diameter with middle cylindrical stage 192 is positioned above stage 192 and has an upwardly divergent sidewall to which is connected an upward cylindrical stage 196. A third or upper frustoconical stage 198 is then connected to upper cylindrical stage 196 with upper stage 198 defining the upper end 184 of flow tube 180. It should be understood that any number of alternating frustoconical stages and cylindrical stages may be conveniently provided, although FIG. 11 shows only three such pairs of alternating stages. It should further be appreciated that the advantage of constructing a flow tube as shown in FIG. 11 resides in the provision of the cylindrical stages between the frustoconical stages since the fluid velocity in each cylindrical stage would be different than the other cylindrical stage and yet for each cylindrical region, the fluid velocity would be constant. This allows a greater accuracy since the fluid velocity may be adjusted so that the gemstone comes to equilibrium in one of the cylindrical stages, that is, in a region where the fluid velocity is constant.

It should be appreciated that other flow tube constructions are within the scope of this invention. For example, a cylindrical tube may be employed wherein the velocity of the fluid therethrough would be constant. For this construction, however, the velocity of the fluid through measurement device 10 would need to be highly adjustable to accommodate gemstones of different specific gravities. In operation with this tube, the fluid flow would be slowly increased until the stone was gradually placed in equilibrium in the fluid. Other possible constructions of the flow tube are contemplated, and these shapes could include any geometrical cross-section as well as any type of sidewall divergence corresponding to any pre-selected mathematical function according to state-of-the-art production capabilities. The advantage of forming the tube in different shapes would be to adapt the tube to peculiar geometries of various gemstones although for most measurements the flow tubes shown in FIGS. 1-11 are quite acceptable.

With construction of a specific gravity measurement apparatus according to the preferred embodiment of the present invention, two basic modes of operation are possible. First, specific gravity may be determined by adjusting the fluid flow rate through the circuit so that the volumetric flow rate is pre-selected to correspond to the weight of the gemstone. In this method, then, the monitoring means or flow tube 12 is calibrated in units of weight in any convenient manner such as on a backing plate or by etching or molding the calibrations on its sidewall. The object of unknown specific gravity is first weighed and then placed in flow tube 14. The flow of fluid is then adjusted to align float F at a position of calibration corresponding to the weight of the object. Flow tube 14 is calibrated for a direct reading of specific gravity which defines a zone wherein the fluid velocity decreases from bottom to top. The specific gravity of the object may then be directly read from the equilibrium position it attains in flow tube 14 since this is directly correlated to its specific gravity.

When gemstones are measured, the $V_o/A_o$ ratio is "built in" to the specific gravity calibrations due to the similarity of geometrical configuration noted above. Thus the device, when operated in this mode, directly indicates specific gravity. The remaining constants in the equilibrium equation are built into the calibration as well, but an added advantage obtains where a similar shape is employed as float F. In this case, the fluid used in the circuit may be changed without affecting the calibration of the device. This is desirable since it is contemplated that different fluids be employed. The reason for incorporating the ability to change fluid is that some gemstones exhibit affinity for certain fluids and this affinity may alter the equilibrium state of the gemstone of unknown specific gravity. By changing the fluid it is possible to prevent the equilibrium position from going unstable since differing fluids have differing Reynold's numbers. Hence the ability to change fluid allows the change of Reynold's number for the system.

A second mode of operation is also possible and is as functionally acceptable as is the first mode. In the second mode, the object of unknown specific gravity, such as a gemstone, is placed in flow tube 14. Fluid is then caused to flow through the circuit, and the rate of flow is adjusted until the gemstone attains a positional equilibrium position at a preselected or "standard" location in flow tube 14. Since a preselected equilibrium point is required for this method, it is convenient to use a cylindrical flow tube since an adjustably constant flow velocity is all that is required. After the gemstone is in positional equilibrium, the fluid velocity at that point is determined by any convenient manner. In the preferred embodiment, the position of float F in flow tube 12 indicates fluid velocity, so that flow tube 12 may be calibrated to read an index value which corresponds to fluid velocity at the pre-selected location in flow tube 14. This index value and the weight of the gemstone of unknown specific gravity then permit calculation of specific gravity, and this calculation may conveniently be provided as a set of tables or by means of microprocessor logic with corresponding display having tabulated and stored data is known in the art.

In either of the two modes, where a gemstone deviates from standard geometry, a simple additional table may be provided to yield a weight factor. This table may be formulated to provide a weight factor corresponding to the geometrical dimensions of the gemstone. The value obtained by the measurement method is then only an "apparent value" since the geometry of the gemstone differs from the standard cut, but this "apparent value" when operated on by the weight factor yields the true specific gravity.

Although the present invention has been described with a certain degree of particularity, it is understood that the present disclosure has been made by way of example and that changes in details and structure may be made without departing from the spirit and scope as defined by the appended claims.

I claim:

1. Apparatus for measuring the specific gravity of an object, comprising:
    an upright test chamber having a lower end and an upper end, said test chamber adapted for receiving said object to be measured;
    a fluid circuit interconnecting said upper and lower ends of said test chamber;
    circulating means associated with said fluid circuit for circulating a viscous fluid through said test chamber in a direction from said lower to said upper end;
    regulating means associated with said fluid circuit for adjusting the rate of flow therethrough; and monitoring means associated with said fluid circuit for measuring the rate of flow therethrough.

2. Apparatus according to claim 1 including a reservoir associated with said fluid circuit, said reservoir adapted for containing an excess amount of said fluid, said fluid being pumped from said reservoir, through said test chamber and returning to said reservoir.

3. Apparatus according to claim 2 wherein said test chamber includes a drain means connected thereto for draining fluid from said test chamber into said reservoir.

4. Apparatus according to claim 1 wherein said circulating means includes a pump and said regulating means includes a valve position in said fluid circuit upstream of said test chamber.

5. Apparatus according to claim 1 wherein said circulating means includes an electric pump assembly and said regulating means is a rheostat electrically connected to said pump assembly whereby said rheostat controls the speed thereof.

6. Apparatus according to claim 1 wherein said test chamber includes lower screen means at said lower end for preventing said object from exiting the test chamber at said lower end while allowing free flow of fluid therethrough.

7. Apparatus according to claim 1 or 6 wherein said test chamber includes an upper screen means at said upper end for preventing said object from exiting the test chamber at said upper end while allowing free flow of fluid therethrough.

8. Apparatus according to claim 1 wherein said test chamber has an upwardly divergent tapered portion whereby the velocity of said fluid at a selected point in comparison to the fluid velocity at the lower end is inversely proportional to the square of the distance said point is from said lower end.

9. Apparatus according the claim 8 wherein said tapered portion is uniformly tapered and circular in cross-section.

10. Apparatus according to claim 9 wherein said tapered portion is uniformly tapered and oval in cross-section.

11. Apparatus according to claim 9 wherein said tapered portion is defined by a plurality of tapered sidewall sections alternating with a plurality of non-tapered sidewall sections.

12. Apparatus according to claim 1 wherein said test chamber having an upwardly divergent tapered portion whereby the velocity of fluid at a selected point in comparison to the fluid velocity at the lower end is linearly proportional to the distance said point is from said lower end.

13. Apparatus according to claim 1 wherein said monitoring means is a tapered tube member defined by an inverted frustum vertically oriented in said fluid circuit having a fluid entrance opening at its lower end and a fluid exit opening at its upper end, said fluid flowing through said tapered member in an upward direction, and a float member positioned in said tapered tube member, said tapered tube being calibrated whereby the relative position of said float in said tapered tube member is indicative of the rate of fluid flow therethrough.

14. Apparatus according to claim 13 wherein said tapered tube is calibrated in units of weight of the object whereby the rate of fluid flow is adjustable to position said float at a calibrated point on said tapered tube corresponding to the object's weight.

15. Apparatus according to claim 13 wherein said tapered tube is calibrated in specific gravity indices, said test chamber having a calibrated equilibrium point whereby the position of said float in said tapered tube for a fluid flow rate maintaining said object at said calibrated equilibrium point is readable as a specific gravity index.

16. Apparatus for measuring the specific gravity of a relatively small object such as a gemstone and the like, comprising:
    first and second chambers vertically mounted in a housing, said first and second chambers each having a tapered portion with upwardly divergent sidewalls and being mounted in juxtaposed relation;
    a reservoir mounted in said housing at a position beneath said chambers; and a fluid circuit including pump means therefor mounted in said housing for circulating fluid through said fluid circuit, said fluid circuit having a first conduit interconnecting said pump means and said reservoir, a second conduit interconnecting said pump means and a lower portion of said first chamber, a third conduit interconnecting an upper portion of said first chamber with a lower portion of said second chamber and a fourth conduit interconnecting an upper portion of said second chamber with said reservoir whereby fluid may be circulated through said fluid cirucit and passing in an upward direction through both said first and second chambers.

17. Apparatus according to claim 16 including a viscous fluid of known specific gravity in said reservoir, said reservoir being of larger volume than the combined volumes of said chambers, and said first, second, third and fourth conduits.

18. Apparatus according to claim 16 including a valve means associated with said second conduit in said fluid circuit for controlling the amount of fluid flow therethrough.

19. Apparatus according to claim 16 including pivot means at the lower ends of each said first and second chambers, said pivot means for allowing each said first and second chambers to be pivoted outwardly of said housing at an angle to the vertical plane defined by said first and second chambers when they are oriented vertically.

20. Apparatus according to claim 19 including first and second releasable seals releasably securing said third conduit to said first chamber upper end and said fourth conduit to said second chamber upper end, respectively.

21. The method of determining the specific gravity of an object comprising the steps of:
   weighing the object;
   placing the object in a vertically upwardly moving stream of fluid in a vertical test chamber having an increasing cross-sectional area from its lower end to its upper end so that the velocity of the fluid varies along its vertical length from a maximum velocity at a lower portion to a minimum velocity at an upper portion to define a zone of varying fluid velocity;
   adjusting the volumetric rate of flow of fluid through said chamber to alter said maximum and minimum velocities, said adjusting of the rate of flow being correlated to the weight of the object whereby said object reaches an equilibrium positional state in said zone; and
   correlating the location of said object in said zone to its specific gravity.

22. The method according to claim 21 wherein said object is symmetrical about its vertical axis when in said equilibrium positional state, said step of correlating the location of the object incorporates a weight factor determined from the ratio of the object's greatest dimension in a horizontal direction to the object's length along said vertical axis.

23. The method of determining the specific gravity of an object of substantially uniform unknown specific gravity comprising the steps of:
   weighing the object;
   placing the object in a vertically upwardly moving stream of fluid in a vertically oriented chamber;
   adjusting the rate of fluid flow through said chamber and measuring the rate of flow of fluid necessary to maintain said object in a state of positional equilibrium at a pre-selected location in said chamber; and
   correlating the rate of flow of fluid necessary to maintain said state of positional equilibrium to the weight of said object to yield its specific gravity.

24. The method according to claim 23 including the step of measuring the flow rate by placing a float of known specific gravity and geometric similarity with said object in a vertically upwardly moving stream of said fluid.

* * * * *